United States Patent [19]
Dorigatti et al.

[11] Patent Number: 5,622,707
[45] Date of Patent: Apr. 22, 1997

[54] COMPOSITE MEMBRANES FOR THE GUIDED REGENERATION OF TISSUES

[75] Inventors: Franco Dorigatti, Lavis; Lanfranco Callegaro, Ponte di Brenta; Aurelio Romeo, Rome, all of Italy

[73] Assignee: M.U.R.S.T. (Italian Ministry for Universities and Scientific and Technological Research), Rome, Italy

[21] Appl. No.: 992,697

[22] Filed: Dec. 18, 1992

[30] Foreign Application Priority Data

Dec. 18, 1991 [IT] Italy .................. PD91A0228

[51] Int. Cl.$^6$ .................. A61K 9/70; A61K 31/00
[52] U.S. Cl. .................. 424/402; 424/404; 424/444; 424/486; 424/488; 428/113; 602/44; 602/45; 442/43
[58] Field of Search .................. 424/486, 488, 424/444; 428/113; 606/228, 230

[56] References Cited

U.S. PATENT DOCUMENTS

| | | | |
|---|---|---|---|
| 4,280,954 | 7/1981 | Yannas et al. | 260/123.7 |
| 4,851,521 | 7/1989 | Della Valle et al. | 536/55.1 |
| 4,965,353 | 10/1990 | Della Valle et al. | 536/55.1 |
| 5,147,861 | 9/1992 | Della Valle et al. | 536/55.1 |

FOREIGN PATENT DOCUMENTS

| | | |
|---|---|---|
| 0138572 | 4/1985 | European Pat. Off. |
| 0216453 | 4/1987 | European Pat. Off. |
| 0251905 | 1/1988 | European Pat. Off. |
| 0265116 | 4/1988 | European Pat. Off. |
| 0341745 | 11/1989 | European Pat. Off. |
| 2268765 | of 1990 | Japan . |
| 2103993 | 3/1983 | United Kingdom . |
| 8810123 | 12/1988 | WIPO . |
| 9117744 | 11/1991 | WIPO . |
| 9213579 | 8/1992 | WIPO . |

OTHER PUBLICATIONS

P.H. Weigel et al J. Theor. Biol., vol. 119 (1986) pp. 219–234.
R.H. Cundiff et al Analytical Chemistry, vol. 33 (1961) pp. 1028–1030.
Database WPIL, Week 8709, Derwent Publications Ltd., London, GB, AN 87–062629 & ZA, A, 8 605 071 (Fidia S.P.A.) 8 Jul. 1987).
R. Cortivo et al., Biomaterials, vol. 12, No. 8, Oct. 1991.

*Primary Examiner*—Edward J. Webman
*Attorney, Agent, or Firm*—Birch, Stewart, Kolasch & Birch, LLP

[57] ABSTRACT

Biomaterials are disclosed comprised of biodegradable, biocompatible, and bioabsorbable composite membranes for use in surgery for the guided regeneration of tissues. The composite membranes are comprised of threads embedded in a matrix, wherein both the matrix and the threads can be comprised of esters of hyaluronic acid, used singly or in combination, or esters of hyaluronic acid in combination with esters of alginic acid or other polymers.

27 Claims, 3 Drawing Sheets

COMPOSITE MEMBRANES FOR THE GUIDED REGENERATION OF TISSUES

BACKGROUND OF THE INVENTION

1. Field of the Invention

The present invention relates to a new biomaterial, called a composite membrane, formed from hyaluronic acid derivatives, processes for its production, and the use of such composite membranes in surgery for the guided regeneration of tissues in the treatment of superficial and internal lesions.

2. Description of Related Art

Hyaluronic acid is a natural heteropolysaccharide composed of alternating residues of D-glucuronic acid and N-acetyl-D-glucosamine. It is a linear polymer with a molecular weight of between 50,000 and 13,000,000 depending upon the source from which it is obtained, and the preparation and determination methods employed. It is present in nature in pericellular gels, in the fundamental substance of connective tissues of vertebrate organisms of which it is one of the main components, in the synovial fluid of joints, in the vitreous humor, in human umbilical cord tissues, and in cocks' combs.

There are known, specific fractions of hyaluronic acid with definite molecular weights that do not present inflammatory activity and which can therefore be used to facilitate wound healing, or to substitute for the endobulbar fluids, or which can be used in therapy for joint pathologies by intra-articular injections as described in European Patent No. 0 138 572 granted to Applicants on Jul. 25, 1990.

Also known are hyaluronic acid esters, wherein all or some of the carboxy groups of the acid are esterified, their use in the pharmaceutical and cosmetic fields and in the area of biodegradable plastic materials, as described in U.S. Pat. Nos. 4,851,521, 4,965,353, and 5,147,861 granted to Applicants, and in European Patent Application 0 251 905 A2, published on Jan. 7, 1988.

Hyaluronic acid is known to play a fundamental role in tissue repair processes, especially in the first stages of granulation, by stabilizing the coagulation matrix and controlling its degradation, favoring the recruitment of inflammatory cells such as polymorphonuclear leukocytes and monocytes, of mesenchymal cells such as fibroblasts and the endothelial cells, and orienting the subsequent migration of epithelial cells.

It is known that the application of solutions of hyaluronic acid can accelerate healing in patients affected by bedsores, wounds and burns.

The role of hyaluronic acid in the various phases that constitute tissue repair processes have been described, by the construction of a theoretical model, by Weigel P. H. et al.: "A model for the role of hyaluronic acid and fibrin in the early events during the inflammatory response and wound healing," *J. Theor. Biol.*, 119: 219, 1986.

Studies aimed at obtaining manufactured products to apply to the skin, composed of hyaluronic acid esters as such or in mixtures with other polymers, have led to the creation of various types of products. Among these are tissues, such as gauzes of varying thickness (number of threads per centimeter), with varying dimensions and with threads of varying denier (weight per 9000 meters of thread).

Films of widely varying thickness have been proposed as described in U.S. Pat. Nos. 4,851,521 and 4,965,353.

One of the limitations to the use of manufactured products composed of hyaluronic acid esters or mixtures of the same with other polymers is their low mechanical resistance, which may cause various problems with their use. In the case of biomaterials, such as membranes or other types of film-forming products, that have to be sewn in place, surgical needles or suture threads can give rise to cracks, cuts or lacerations that jeopardize the structural soundness of the membrane, and consequently the stability of the membrane in its place of application, thus laying the wound open to contamination and undesirable consequences.

Modern surgery now tends to employ, wherever possible, biomaterials with high biocompatibility, such as those obtained from hyaluronic acid esters, characterized also by high biodegradability and bioabsorbability.

SUMMARY OF THE INVENTION

Objects of the present invention include methods of preparing, characterizing, and using composite, biocompatible and bioabsorbable membranes, comprising hyaluronic acid esters used singly or in mixtures. Compared to other membranes obtained from the same hyaluronic acid esters, these composite membranes possess superior properties with respect to mechanical resistance to tension and physical and mechanical tearing, even where suture stitches are used or other means of securing in general use in surgical practice for the application of biomaterials inside or on the surface of the human body are employed. Apart from these new mechanical properties, such composite membranes are also highly biocompatible and biodegradable.

The composite membranes of the present invention may comprise hyaluronic acid esters used singly or in mixtures, alginic acid esters used singly or in combination, and mixed membranes comprising hyaluronic acid esters and alginic acid esters in combination, or such esters used in combination with other polymers.

Further scope of the applicability of the present invention will become apparent from the detailed description and drawings provided below. However, it should be understood that the detailed description and specific examples, while indicating preferred embodiments of the invention, are given by way of illustration only since various changes and modifications within the spirit and scope of the invention will become apparent to those skilled in the art from this detailed description.

BRIEF DESCRIPTION OF THE DRAWINGS

The above and other objects, features, and advantages of the present invention will be better understood from the following detailed descriptions taken in conjunction with the accompanying drawings, all of which are given by way of illustration only, and are not limitative of the present invention, in which.

DETAILED DESCRIPTION OF THE INVENTION

The following detailed description of the invention is provided to aid those skilled in the art in practicing the present invention. Even so, the following detailed description should not be construed to unduly limit the present invention, as modifications and variations in the embodiments herein discussed may be made by those of ordinary skill in the art without departing from the spirit or scope of the present inventive discovery.

The contents of each of the references cited in the present application are herein incorporated by reference in their entirety.

The aforesaid objects are achieved by providing composite membranes according to the present invention, having a basis weight between about 8 gr/cm² and about 50 gr/cm², with a thickness when dry between about 0.08 mm and about 0.5 mm, a minimum tensile strength at break when dry of about 100 Kg/cm² to about 1000 Kg/cm², an elongation when dry between about 3% and about 12%, a minimum tensile strength at break when wet between about 30 Kg/cm² and about 450 Kg/cm², and an elongation when wet between about 20% and about 60%, a tear strength when dry of about 40 Kg/cm² to about 200 Kg/cm², and when wet of about 20 Kg/cm² to about 160 Kg/cm².

The composite membrane of the present invention is a composite structure comprising a polymeric matrix in which a mesh reinforcement comprising a material the same as or different from the matrix has been embedded. The reinforcing structure, which guards against the spread of cracks or tears caused by suture threads or surgical needles, comprises a multiple and possibly twisted thread, produced by extrusion under dry or wet conditions, knitted into a fabric with a gauge between about 10 and about 16.

The multiple thread is composed of between about 30 and about 120 filaments (strands) between about 18 microns and about 35 microns in diameter, and between about 150 and about 400 denier.

The polymeric matrix and the inner reinforcing mesh can comprise hyaluronic acid esters as described in U.S. Pat. Nos. 4,851,521 and 4,965,353, and in PCT publication WO 92-13579, used singly or in mixtures with each other in varying percentages.

Moreover, the polymeric matrix, in which is embedded the mesh reinforcement, can comprise mixtures of one or more hyaluronic acid esters in addition to biologically and pharmacologically active principles of gelled polysaccharides such as chitin, alginates, chitosan, gellan, and their synthetic or semisynthetic derivatives.

The present composite membranes are unique in that they are entirely biocompatible and biodegradable since they are composed, internally and externally, of materials possessing such characteristics. The composite structure, i.e., the mesh/polymeric matrix, comprises a single mass wherein the two component parts are inseparable, even under wet conditions. This is a result of the coating technique used on the reinforcing mesh, wherein the polymeric coating solution contains a solubilization solvent, which is also a solvent used for producing the material comprising the reinforcing mesh. The solubilization solvent acts on the mesh, creating a chemical link between the polymeric matrix and the reinforcing mesh. The final product is a single article comprising the two combined structures.

The present composite membranes are also unique because it is possible to modulate the resistance and stiffness characteristics of the material under wet conditions. This can be achieved by inserting biocompatible and bioabsorbable reinforcement meshes constituting a single body within the polymeric matrix. Thus, different mechanical performance can be achieved by employing different materials with varying intrinsic properties constituting the threads. For example, with respect to HYAFF 11 and ALAFF 11, the properties of these threads can be summarized as follows:

|          | Tensile Strength (MPa) | Elongation (%) | Young Modulus (MPa) |
| --- | --- | --- | --- |
| HYAFF 11 | 39  | 96  | 560  |
| ALAFF 11 | 183 | 15  | 5428 |

Thus, the composite membranes of the present invention possess the advantage that the stiffness of the inner mesh can be modulated, according to need, while guaranteeing the integrity of the final product. Conventional composite materials for biomedical use comprising reinforcement meshes in polymeric matrices possess the drawback that the two components possess different mechanical characteristics, and are therefore prone to becoming separated under, for example, wet conditions.

The composite membranes of the present invention possess the advantage that, while being made of materials with different chemical/physical characteristics, they do not suffer from the drawback of becoming separated in use.

Figure 1:
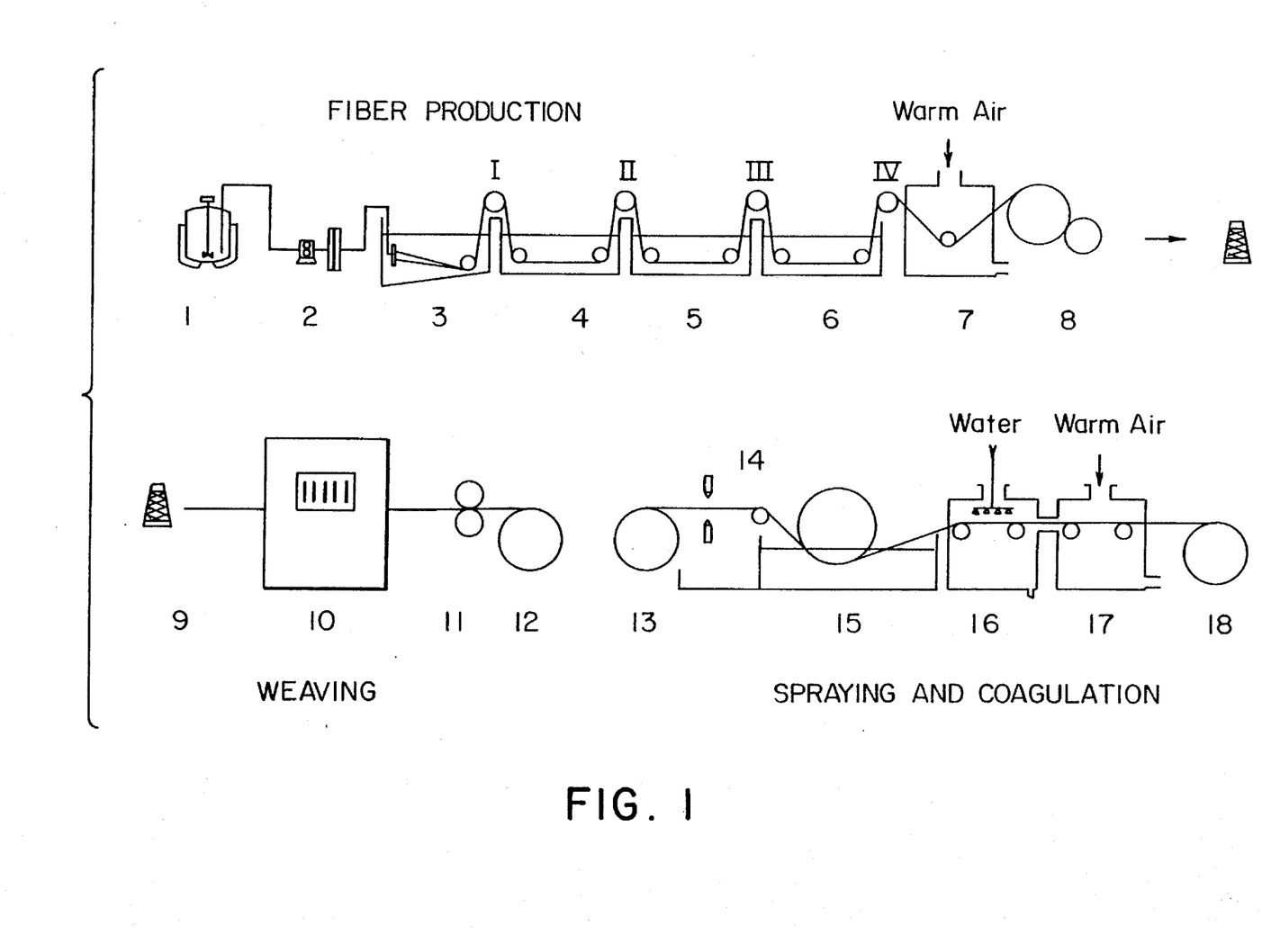
FIG. 1 is a schematic diagram illustrating the steps involved in the production of the composite membranes of the present invention.

The composite membranes with the aforesaid characteristics can be produced starting from a mesh reinforcement constructed as follows. With reference to FIG. 1, a polymer solution at a concentration of between about 80 mg/ml and about 180 mg/ml is prepared in a vessel (1), is fed by a gear metering pump (2) into a spinneret for wet extrusion with between about 30 and about 120 holes, each measuring between about 55 microns and about 140 microns in diameter. The multiple thread extruded therefrom passes into a coagulating bath (3) and is then moved across transporting rollers into three successive baths where it is rinsed (4,5,6). The ratio between the speed of the third roller (III) and that of the first roller (I) is called the drafting ratio, and varies between about 1 and about 1.3, while the speed of the rollers varies between about 2 and about 30 rpm (revolutions per minute). Once it has been passed through the rinsing baths, the multiple thread is dried with warm air (7) at a temperature varying between about 40° C. and about 55° C., and is then wound onto a winding frame (8). The denier of the thread varies between about 150 and about 400 denier. The multiple thread is then twisted between about 90 and about 200 times per meter and woven on a loom into a smooth knitted fabric with a gauge of between about 10 and about 16 (9,10). When it comes off the loom, the fabric is fed through a calendar (11) which thins it down. The polymeric matrix is fed between two airbrushes (14) which spray it with a polymer solution at a concentration of between about 30 mg/ml and about 120 mg/ml. The solvent which can be employed to form this polymer solution can be an aprotic solvent, and can include an amide of a carboxylic acid, especially a dialkylamide of an aliphatic acid with between 1 and 5 carbon atoms and deriving from alkyl groups with between 1 and 6 carbon atoms, and from an organic sulfoxide, that is, a dialkylsulfoxide with alkyl groups with a maximum of 6 carbon atoms, such as especially, dimethylsulfoxide or diethylsulfoxide, and by a fluorinated solvent with a lower boiling point, such as hexafluoro-isopropanol. N-methyl pyrrolidone is also useful. The sprayed mesh passes into a coagulation bath (15), into a washing chamber (16), and into a heated roller drying chamber with a temperature varying between about 40° C. and about 55° C. (17).

The coagulation baths 3 and 15 are stainless steel, and are in the form of an upturned triangle so that the extracted solubilization solvent can be deposited in the deepest part thereof, while the material being formed can be kept in contact with fresh coagulation solvent.

The coagulation process is essentially an extraction process by which, from a solution of polymer and solvent, the extraction of the solubilization solvent and the solidification of the polymer can be effected by the addition of a second solvent, for example ethanol, in which the solubilization solvent, for example dimethylsulfoxide, is soluble, and the polymer is insoluble.

The present invention therefore relates to a new class of product to be used in the medical/pharmaceutical field for the treatment of internal or superficial lesions. The product is known as a "composite membrane," and is totally or partially biocompatible and bioabsorbable. It is composed of hyaluronic acid esters, singly or mixed together with other natural, synthetic or semisynthetic polymers. Such materials exhibit high mechanical resistance, especially to tearing, which tends to occur in surgery when membranes are fixed to the tissues surrounding the operated area.

The greater mechanical resistance of the present composite membranes compared to membranes obtained by simple extrusion can be determined by mechanical characterization. To demonstrate this, a comparison was conducted between a continuous membrane of hyaluronic acid ethyl ester and a composite membrane with a hyaluronic acid ethyl ester mesh and a matrix of hyaluronic acid benzyl ester. The comparison yielded the results shown in Table 1.

TABLE 1

| | TYPE OF MEMBRANE | | | |
|---|---|---|---|---|
| | CONTINUOUS | | COMPOSITE | |
| | DRY | WET | DRY | WET |
| THICKNESS (um) | 18.8 | 60 | 195 | 400 |
| MIN. TENSILE STRENGTH AT BREAK (Kg/cm$^2$) | 1000 | 40 | 650 | 120 |
| ELONGATION (%) | 6 | 42 | 7 | 50 |
| TEAR STRENGTH (Kg/cm$^2$) | 15 | 8 | 90 | 50 |

Tear strength was measured by passing an 8/0 suture thread through the membrane with a surgical needle.

These data demonstrate that under wet conditions (working conditions) the mechanical characteristics of the composite membrane of the present invention are markedly better than those of the traditional, continuous membrane.

The Esters of Hyaluronic Acid

Esters of hyaluronic acid useful in the present invention are esters of hyaluronic acid with aliphatic, araliphatic, cycloaliphatic or heterocyclic alcohols, in which are esterified all (so-called "total esters") or only a part (so-called "partial esters") of the carboxylic groups of the hyaluronic acid, and salts of the partial esters with metals or with organic bases, biocompatible or acceptable from a pharmacological point of view.

The useful esters include esters which derive from alcohols which themselves possess a notable pharmacological action. The saturated alcohols of the aliphatic series or simple alcohols of the cycloaliphatic series are useful in the present invention.

In the above mentioned esters in which some of the carboxylic acid groups remain free (i.e., partial esters), these may be salified with metals or organic bass, such as with alkaline or alkaline earth metals or with ammonia or nitrogenous organic bases.

Most of the esters of hyaluronic acid ("HY"), unlike HY itself, present a certain degree of solubility in organic solvents. This solubility depends on the percentage of esterified carboxylic groups and on the type of alkyl group linked with the carboxyl. Therefore, an HY compound with all its carboxylic groups esterified presents, at room temperature, good solubility for example in dimethylsulfoxide (the benzyl ester of HY dissolves in DMSO in a measure of 200 mg/ml). Most of the total esters of HY present also, unlike HY and especially its salts, poor solubility in water and are essentially insoluble in water. The solubility characteristics, together with particular and notable viscoelastic properties, make the HY esters particularly preferred for use in composite membranes.

Alcohols of the aliphatic series to be used as esterifying components of the carboxylic groups of hyaluronic acid for use in composite membranes according to the present invention are for example those with a maximum of 34 carbon atoms, which may be saturated or unsaturated and which may possibly also be substituted by other free functional or functionally modified groups, such as amine, hydroxyl, aldehyde, ketone, mercaptan, or carboxyl groups or by groups derived from these, such as hydrocarbyl or dihydrocarbylamine groups (from now on the term "hydrocarbyl" will be used to refer not only to monovalent radicals of hydrocarbons such as the $C_nH_{2n+1}$ type, but also bivalent or trivalent radicals, such as "alkylenes" $C_nH_{2n-1}$ or "alkylidenes" $C_nH_{2n}$), ether or ester groups, acetal or ketal groups, thioether or thioester groups, and esterified carboxyl or carbamide groups and carbamide substituted by one or more hydrocarbyl groups, by nitrile groups or by halogens.

Of the above mentioned groups containing hydrocarbyl radicals, these are preferably lower aliphatic radicals, such as alkyls, with a maximum of 6 carbon atoms. Such alcohols may also be interrupted in the carbon atom chain by heteroatoms, such as oxygen, nitrogen and sulfur atoms. Preferred are alcohols substituted with one or two of the said functional groups.

Alcohols of the above mentioned group which are preferably used are those with a maximum of 12, and especially 6 carbon atoms, and in which the hydrocarbyl atoms in the above mentioned amine, ether, ester, thioether, thioester, acetal, ketal groups represent alkyl groups with a maximum of 4 carbon atoms, and also in the esterified carboxyl or substituted carbamide groups the hydrocarbyl groups are alkyls with the same number of carbon atoms, and in which in the amine or carbamide groups may be alkylenamine or alkylenecarbamide groups with a maximum of 8 carbon atoms. Of these alcohols, specifically preferred are saturated and non-substituted alcohols, such as the methyl, ethyl, propyl, and isopropyl alcohols, normal butyl alcohol, isobutyl alcohol, tertiary butyl alcohol, the amyl, pentyl, hexyl, octyl, nonyl and dodecyl alcohols and, above all, those with a linear chain, such as normal octyl and dodecyl alcohols. Of the substituted alcohols of this group, the bivalent alcohols are useful, such as ethyleneglycol, propyleneglycol and butyleneglycol, the trivalent alcohols such as glycerine, the aldehyde alcohols such as tartronic alcohol, the carboxylic alcohols such as lactic acids, for example glycolic acid, malic acid, the tartaric acids, citric acid, the aminoalcohols, such as normal aminoethanol, aminopropanol, normal aminobutanol and their dimethylated and diethylated derivatives in the amine function, choline, pyrrolidinylethanol, piperidinylethanol, piperazinylethanol and the corresponding derivatives of normal propyl or normal butyl alcohol, monothioethyleneglycol or its alkyl derivatives, such as the ethyl derivative in the mercaptan function.

Of the higher saturated aliphatic alcohols, preferred are cetyl alcohol and myricyl alcohol, but for the aim of the present invention the higher unsaturated alcohols with one or two double bonds, are especially important, such as especially those contained in many essential oils and related to terpenes, such as citronellol, geraniol, nerol, nerolidol, linalool, farnesol, and phytol. Of the unsaturated lower alcohols it is necessary to consider allyl alcohol and propargyl alcohol. Of the araliphatic alcohols, preferred are those with only one benzene residue and in which the aliphatic chain has a maximum of 4 carbon atoms, in which the benzene residue can be substituted by between 1 and 3 methyl or hydroxyl groups or by halogen atoms, especially by chlorine, bromine and iodine, and in which the aliphatic chain may be substituted by one or more functions chosen from the group containing free amine groups or mono- or dimethylated or by pyrrolidine or piperidine groups. Of these alcohols, most preferred are benzyl alcohol and phenetyl alcohol.

The alcohols of the cycloaliphatic or aliphatic-cycloaliphatic series may derive from mono- or polycyclic hydrocarbons, may preferably have a maximum of 34 carbon atoms, may be unsubstituted and may contain one or more substituents, such as those mentioned above for the aliphatic alcohols. Of the alcohols derived from cyclic monoannular hdrocarbons, preferred are those with a maximum of 12 carbon atoms, the rings with preferably between 5 and 7 carbon atoms, which may be substituted for example by between one and three lower alkyl groups, such as methyl, ethyl, propyl or isopropyl groups. As specific alcohols of this group the following are most preferred: cyclohexanol, cyclohexanediol, 1,2,3-cyclohexanetriol and 1,3,5-cyclohexanetriol (phloroglucitol), inositol, and the alcohols which derive from p-methane such as carvomenthol, menthol, and α-γterpineol, 1-terpineol, 4-terpineol and piperitol, or the mixture of these alcohols known as "terpineol", 1,4- and 1,8 terpin. Of the alcohols which derive from hydrocarbons with condensed rings, such as those of thujane, pinane or comphane, the following are preferred: thujanol, sabinol, pinol hydrate, D and L-borneol and D and L-isoborneol.

Aliphatic-cycloaliphatic polycyclic alcohols to be used for the esters of the present invention are sterols, cholic acids and steroids, such as sexual hormones and their synthetic analogues, especially corticosteroids and their derivatives. It is therefore possible to use: cholesterol, dihydrocholesterol, epidihydrocholesterol, coprostanol, epicoprostanol, sitosterol, stigmasterol, ergosterol, cholic acid, deoxycholic acid, lithocholic acid, estriol, estradiol, equilenin, equilin and their alkylate derivatives, as well as their ethynyl or propynyl derivatives in position 17, such as 17α-ethynlestradiol or 7α-methyl-17α-ethynyl-estradiol, pregnenolone, pregnanediol, testosterone and its derivatives, such as 17α-methyltestosterone, 1,2-dehydrotestosterone and 17α-methyl-1,2-dehydrotesterone, the alkynylate derivatives in position 17 of testosterone and 1,2-dehydrotestosterone, such as 17α-ethynyltestosterone, 17α-propynyltestosterone, norgestrel, hydroxyprogesterone, corticosterone, deoxycorticosterone, 19-nortestosterone, 19-nor-17α-methyltestosterone and 19-nor-17α-ethynyltestosterone, antihormones such as cyproterone, cortisone, hydrocortisone, prednisone, prednisolone, fluorocortisone, dexamethasone, betamethasone, paramethasone, flumethasone, fluocinolone, fluprednylidene, clobetasol, beclomethasone, aldosterone, deoxycorticosterone, alfaxolone, alfadolone, and bolasterone. As esterifying components for the esters of the present invention the following are useful: genins (aglycones) of the cardioactive glucosides, such as digitoxigenin, gitoxigenin, digoxigenin, strophanthidin, tigogenin and saponins.

Other alcohols to be used according to the invention are vitamins, such as axerophthol, vitamins $D_2$ and $D_3$, aneurine, lactoflavine, ascorbic acid, riboflavine, thiamine, and pantothenic acid.

Of the heterocyclic acids, the following can be considered as derivatives of the above mentioned cycloaliphatic or aliphatic-cycloaliphatic alcohols if their linear or cyclic chains are interrupted by one or more, for example, by between one and three heteroatoms, for instance chosen from the group formed by —O—, —S—, —N, and —NH—, and in these, there may be one or more unsaturated bonds, for example double bonds, in particular between one and three, thus including also heterocyclic compounds with aromatic structures. For example the following should be mentioned: furfuryl alcohol, alkaloids and derivatives such as atropine, scopolamine, cinchonine, cinchonidine, quinine, morphine, codeine, nalorphine, N-butylscopolammonium bromide, ajmaline; phenylethylamines such as ephedrine, isoproterenol, epinephrine; phenothiazine drugs such as perphenazine, pipothiazine, carphenazine, homofenazine, acetophenazine, fluophenazine, and N-hydroxyethylpromethazine chloride; thioxanthene drugs such as flupenthixol and clopenthixol; anticonvulsants such as meprophendiol; antipsychotics such as opipramol; antiemetics such as oxypendyl; analgesics such as carbetidine and phenoperidine and methadol; hypnotics such as etodroxizine; anorexics such as benzidrol and diphemethoxidine; minor tranquilizers such as hydroxyzine; muscle relaxants such as cinnamedrine, diphylline, mephenesin, methocarbamol, chlorphenesin, 2,2-diethyl-1,3-propanediol, guaifenesin, hydrocilamide; coronary vasodilators such as dipyridamole and oxyfedrine; adrenergic blockers such as propanolol, timolol, pindolol, bupranolol, atenolol, metroprolol, practolol; antineoplastics such as 6-azauridine, cytarabine, floxuridine; antibiotics such as chloramphenicol, thiamphenicol, erythromycin, oleandomycin, lincomycin; antivirals such as idoxuridine; peripheral vasodilators such as isonicotinyl alcohol; carbonic anhydrase inhibitors such as sulocarbilate; antiasthmatics and antiinflammatories such as tiaramide; sulfamidics such as 2-p-sulfanilonoethanol.

In some cases hyaluronic acid esters may be of interest where the ester groups derive from two or more therapeutically active hydroxylic substances, and naturally all possible variants may be obtained. Especially interesting are the substances in which two types of different ester groups deriving from drugs of a hydroxylic character are present and in which the remaining carboxyl groups are free, salified with metals or with a base, possibly also the bases being themselves therapeutically active, for example with the same or similar activity as that of the esterifying component. In particular, it is possible to have hyaluronic esters deriving on the one hand from an antiinflammatory steroid, such as one of those mentioned previously, and on the other hand from a vitamin, from an alkaloid or from an antibiotic, such as one of those listed.

Method of Preparing HY Esters of the Invention

Method A:

The esters of hyaluronic acid may be prepared by methods known per se for the esterification of carboxylic acids, for example by treatment of free hyaluronic acid with the desired alcohols in the presence of catalyzing substances, such as strong inorganic acids or ionic exchangers of the acid type, or with an etherifying agent capable of introducing the desired alcoholic residue in the presence of inorganic or organic bases. As esterifying agents it is possible to use those known in literature, such as especially the esters of various inorganic acids or of organic sulphonic acids, such as hydracids, that is hydrocarbyl halogenides, such as methyl or ethyl iodide, or neutral sulphates or hydrocarbyl acids, alfites, carbonates, silicates, phosphites or hydrocarbyl sulfonates, such as methyl benzene or p-toluene-sulfonate or methyl or ethyl chlorosulfonate. The reaction may take place in a suitable solvent, for example an alcohol, preferably that corresponding to the alkyl group to be introduced in the carboxyl group. But the reaction may also take place in non-polar solvents, such as ketones, ethers, such as dioxane or aprotic solvents, such as dimethylsulphoxide. As a base it is possible to use for example a hydrate of an alkaline or alkaline earth metal or magnesium or silver oxide or a basic salt or one of these metals, such as a carbonate, and, of the organic bases, a tertiary azotized base, such as pyridine or collidine. In the place of the base it is also possible to use an ionic exchanger of the basic type.

Another esterification method employs the metal salts or salts with organic azotized bases, for example ammonium or ammonium substitute salts. Preferably, the salts of the alkaline or alkaline earth metals are used, but also any other metallic salt may be used. The esterifying agents are also in this case those mentioned above and the same applies to the solvents. It is preferable to use aprotic solvents, for example dimethylsulphoxide and dimethylformamide.

In the esters obtained according to this procedure or according to the other procedure described hereafter, free carboxylic groups of the partial esters may be salified, if desired, in a per se known manner.

Method B:

The hyaluronic esters may also be prepared by a method which consists of treating a quaternary ammonium salt of hyaluronic acid with an etherifying agent, preferably in an aprotic organic solvent.

As organic solvents it is preferable to use aprotic solvents, such as dialkylsulphoxides, dialkylcarboxamides, such as in particular lower alkyl dialkylsulphoxides, especially dimethyl-sulphoxide, and lower alkyl dialkylamides of lower aliphatic acids, such as dimethyl or diethyl-formamide or dimethyl or diethylacetamide.

Other solvents however are to be considered which are not always aprotic, such as alcohols, ethers, ketones, esters, especially aliphatic or heterocyclic alcohols and ketones with a lower boiling point, such as hexafluoroisopropanol, trifluoroethanol, and N-methylpyrrolidone.

The reaction is effected preferably at a temperature range of between about 0° C. and 100° C., especially between about 25° C. and 75° C., for example at about 30° C.

The esterification is carried out preferably by adding by degrees the esterifying agent to the above mentioned ammonium salt to one of the above mentioned solvents, for example to dimethyl-sulphoxide.

As an alkylating agent it is possible to use those mentioned above, especially the hydrocarbyl halogens, for example alkyl halogens. As starting quaternary ammonium salts it is preferable to use the lower ammonium tetraalkylates, with alkyl groups preferably between 1 and 6 carbon atoms. Mostly, hyaluronate of tetrabutylammonium is used. It is possible to prepare these quaternary ammonium salts by reacting a metallic salt of hyaluronic acid, preferably one of those mentioned above, especially sodium or potassium salt, in aqueous solution with a salified sulphonic resin with a quaternary ammonium base.

One variation of the previously described procedure consists in reacting a potassium or sodium salt of hyaluronic acid, suspended in a suitable solution such as dimethylsulphoxide, with a suitable alkylating agent in the presence of catalytic quantities of a quaternary ammonium salt, such as iodide of tetrabutylammonium.

For the preparation of the hyaluronic acid esters, it is possible to use hyaluronic acids of any origin, such as for example the acids extracted from the above mentioned natural starting materials, for example from cocks' combs. The preparation of such acids is described in literature: preferably, purified hyaluronic acids are used. Especially used are hyaluronic acids comprising molecular fractions of the integral acids obtained directly by extraction of the organic materials with molecular weights varying within a wide range, for example from about 90%–80% (MW= 11.7–10.4 million) to 0.2% (MW=30,000) of the molecular weight of the integral acid having a molecular weight of 13 million, preferably between 5% and 0.2%. Such fractions may be obtained with various procedures described in literature, such as by hydrolyzing, oxydizing, enzymatic or physical procedures, such as mechanical or radiational procedures. Primordial extracts are therefore often formed during these same by publication procedures (for example see the article by Balazs et al. quoted above in "Cosmetics & Toiletries"). The separation and purification of the molecular fractions obtained are brought about by known techniques, for example by molecular filtration.

Additionally useful are purified fractions obtainable from hyaluronic acid, such as for example the ones described in European Patent Publn. No. 0138572.

The salification of HY with the above metals, for the preparation of starting salts for the particular esterification procedure described above, is performed in a per se known manner, for example by reacting HY with the calculated base quantity, for example with alkaline hydrates or with basic salts of such metals, such as carbonates or bicarbonates.

In the partial esters it is possible to salify all the remaining carboxylic groups or only part of them, dosing the base quantities so as to obtain the desired stoichiometric degree of salification. With the correct degree of salification it is possible to obtain esters with a wide range of different dissociation constants and which therefore give the desired pH, in solution or "in situ" at the time of therapeutic application.

PREPARATION EXAMPLES

The following exemplify the preparation of hyaluronic acid esters useful in the composite membranes of the present invention.

Example 1

Preparation of the (Partial) Propyl Ester of Hyaluronic Acid (Hy)

50% of the esterified carboxylic groups
50% of the salified carboxylic groups (Na)

12.4 g of HY tetrabutylammonium salt with a molecular weight 170,000 corresponding to 20 m.Eq. of a monomeric unit are solubilized in 620 ml of dimethylsulfoxide at 25° C., 1.8 g (10.6 m.Eq.) of propyl iodide are added and the resulting solution is kept at a temperature of 30° for 12 hours.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30° C.

The product is then dissolved in 550 ml of water containing 1% of sodium chloride and the solution is slowly poured into 3,000 ml of acetone under constant agitation. A precipitate is formed which is filtered and washed twice with 500 ml of acetone/water (5:1) and three times with 500 ml of acetone and finally vacuum dried for 24 hours at 30° C. 7.9 g of the partial propyl ester compound in the title are obtained. Quantitative determination of the ester groups is carried out using the method of R. H. Cundiff and P. C. Markunas [Anal. Chem. 33, 1028–1030, (1961)].

Example 2

Preparation of the (Partial) Isopropyl Ester of Hyaluronic Acid (HY)—50% of Esterified Carboxylic groups—50% of Salified Carboxylic Groups (Na)

12.4 g of HY tetrabutylammonium salt with a molecular weight of 160,000 corresponding to 20 m.Eq. of a monomeric unit are solubilized in 620 ml of dimethylsulfoxide at 25° C., 1.8 g (10.6 m.Eq.) of isopropyl iodide are added and the resulting solution is kept for 12 hours at 30° C.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30° C.

The product is then dissolved in 550 ml of water containing 1% of sodium chloride and the solution is slowly poured into 3,000 ml of acetone under constant agitation. A precipitate is formed which is filtered and washed twice with 500 ml of acetone/water 5:1 and three times with 500 ml of acetone and finally vacuum dried for 24 hours at 30° C. 7.8 g of the partial isopropyl ester compound in the title are obtained. Quantitative determination of the ester groups is carried out using the method of R. H. Cundiff and P. C. Markunas [Anal. Chem. 33, 1028–1030 (1961)].

Example 3

Preparation of the (Partial) Ethyl Ester of Hyaluronic Acid (HY)—75% of Esterified Carboxylic Groups—25% of Salified Carboxylic Groups (Na)

12.4 g of HY tetrabutylammonium salt with a molecular weight of 250,000 corresponding to 20 m.Eq. of a monomeric unit are solubilized in 620 ml of dimethylsulfoxide at 25° C., 2.5 g (15.9 m.Eq.) of ethyl iodide are added and the resulting solution is kept for 12 hours at 30° C.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30° C.

The product is then dissolved in 550 ml of water containing 1% of sodium chloride and the solution is slowly poured into 3,000 ml of acetone under constant agitation. A precipitate is formed which is filtered and washed twice with 500 ml of acetone/water 5:1 and three times with 500 ml of acetone and finally vacuum dried for 24 hours at 30° C. 7.9 g of the partial ethyl ester compound in the title are obtained. Quantitative determination of the ester groups is carried out using the method of R. H. Cundiff and P. C. Markunas [Anal. Chem. 33, 1028–1030, (1961)].

Example 4

Preparation of the (Partial) Methyl Ester of Hyaluronic Acid (HY)—75% of Esterified Carboxylic Groups—25% of Salified Carboxylic Groups (Na)

12.4 g or HY tetrabutylammonium salt with a molecular weight of 80,000 corresponding to 20 m.Eq. of a monomeric unit are solubilized in 620 ml of dimethylsulfoxide at 25° C., 2.26 g (15.9 m.Eq.) of methyl iodide are added and the resulting solution is kept for 12 hours at 30° C.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30° C.

The product is then dissolved in 550 ml of water containing 1% of sodium chloride and the solution is slowly poured into 3,000 ml of acetone under constant agitation. A precipitate is formed which is filtered and washed twice with 500 ml of acetone/water 5:1 and three times with 500 ml of acetone and finally vacuum dried for 24 hours at 30° C. 7.8 g of the partial methyl ester compound in the title are obtained. Quantitative determination of the ester groups is carried out using the method of R. H. Cundiff and P. C. Markunas [Anal. Chem. 33, 1028–1030 (1961)].

Example 5

Preparation of the Methyl Ester of Hyaluronic Acid (HY)

12.4 g of HY tetrabutylammonium salt with a molecular weight of 120,000 corresponding to 20 m.Eq. of a monomeric unit are solubilized in 620 ml of dimethylsulfoxide at 25° C., 3 g (21.2 m.Eq.) of methyl iodide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for twenty four hours at 30° C.

8 g of the ethyl ester product in the title are obtained. Quantitative determination of the ester groups is carried out using the method of R. H. Cundiff and P. C. Markunas [Anal. Chem. 33, 1028–1030 (1961)].

Example 6

Preparation of the Ethyl Ester of Hyaluronic Acid (HY)

12.4 g of HY tetrabutylammonium salt with a molecular weight of 85,000 corresponding to 20 m.Eq. of a monomeric unit are solubilized in 620 ml of dimethylsulfoxide at 25° C., 3.3 g (21.2 m.Eq.) of ethyl iodide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for twenty-four hours at 30° C.

8 g of the ethyl ester product in the title are obtained. Quantitative determination of the ester groups is carried out using the method of R. H. Cundiff and P. C. Markunas [Anal. Chem. 33, 1028–1030 (1961)].

Example 7

Preparation of the Propyl Ester of Hyaluronic Acid (HY)

12.4 g of HY tetrabutylammonium salt with a molecular weight of 170,000 corresponding to 20 m.Eq. of a monomeric unit are solubilized in 620 ml of dimethylsulfoxide at 25° C., 3.6 g (21.2 m.Eq.) of propyl iodide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for twenty-four hours at 30° C.

8.3 g of the propyl ester product in the title are obtained. Quantitative determination of the ester groups is carried out using the method of R. H. Cundiff and P. C. Markunas [Anal. Chem. 33, 1028–1030 (1961)].

Example 8

Preparation of the (Partial) Butyl Ester of Hyaluronic Acid (HY)—50% of Esterified Carboxylic Groups—50% of Salified Carboxylic Groups (Na)

12.4 g of HY tetrabutylammonium salt with a molecular weight of 620,000 corresponding to 20 m.Eq. of a monomeric unit are solubilized in 620 ml of dimethylsulfoxide at 25° C., 1.95 g (10.6 m.Eq.) of n-butyl iodide are added and the resulting solution is kept for 12 hours at 30° C.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30° C.

The product is then dissolved in 550 ml of water containing 1% of sodium chloride and the solution is slowly poured into 3,000 ml of acetone under constant agitation. A precipitate is formed which is filtered and washed twice with 500 ml of acetone/water 5:1 and three times with 500 ml of acetone and finally vacuum dried for 24 hours at 30° C. 8 g of the partial butyl ester compound in the title are obtained. Quantitative determination of the ester groups is carried out using the method of R. H. Cundiff and P. C. Markunas [Anal. Chem. 33, 1028–1030 (1961)].

Example 9

Preparation of the (Partial) Ethoxycarbonylmethyl Ester of Hyaluronic Acid (HY)—75% of Esterified Carboxylic Groups—25% of Salified Carboxylic Groups (Na)

12.4 g of HY tetrabutylammonium salt with a molecular weight of 180,000 corresponding to 20 m.Eq. of a monomeric unit are solubilized in 620 ml of dimethylsulfoxide at 25° C., 2 g of tetrabutylammonium iodide and 1.84 g (15 m.Eq.) of ethyl chloroacetate are added and the resulting solution of kept for 24 hours at 30° C.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30° C.

The product is then dissolved in 550 ml of water containing 1% of sodium chloride and the solution is slowly poured into 3,000 ml of acetone under constant agitation. A precipitate is formed which is filtered and washed twice with 500 ml of acetone/water 5:1 and three times with 500 ml of acetone and finally vacuum dried for 24 hours at 30° C. 10 g of the partial ethoxycarbonyl methyl ester compound in the title are obtained.

Quantitative determination of the ethoxylic ester groups is carried out using the method of R. H. Cundiff and P. C. Markunas [Anal. Chem. 33, 1028–1030 (1961)].

Example 10

Preparation of the N-pentyl Ester of Hyaluronic Acid (HY)

12.4 g of HY tetrabutylammonium salt with a molecular weight of 620,000 corresponding to 20 m.Eq. of a monomeric unit are solubilized in 620 ml of dimethylsulfoxide at 25° C., 3.8 g (25 m.Eq.) of n-pentyl bromide and 0.2 g of iodide tetrabutyl-ammonium are added, the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for twenty four hours at 30° C.

8.7 g of the n-pentyl ester product in the title are obtained. Quantitative determination of the ester groups is carried out using the method described on pages 169–172 of Siggia S. and Hann J. G. "Quantitative organic analysis via functional groups" 4th Edition, John Wiley and Sons.

Example 11

Preparation of the Isopentyl Ester of Hyaluronic Acid (HY)

12.4 g of HY tetrabutylammonium salt with a molecular weight of 170,000 corresponding to 20 m.Eq. of a monomeric unit are solubilized in 620 ml of dimethysulfoxide at 25° C., 3.8 g (25 m.Eq.) of isopentyl bromide and 0.2 g of tetrabutylammonium iodide are added, the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for twenty four hours at 30° C.

8.6 g of the isopentyl ester product featured in the title are obtained. Quantitative determination of the ester groups is carried out according to the method described on pages 169–172 of Siggia S. and Hanna J. G. "Quantitative organic analysis via functional groups" 4th Edition, John Wiley and Sons.

Example 12

Preparation of the Benzylester of Hyaluronic Acid (HY)

12.4 g of HY tetrabutylammonium salt with a molecular weight of 170,000 corresponding to 20 m.Eq. of a monomeric unit are solubilized in 620 ml of dimethylsulfoxide at 25° C., 4.5 g (25 m. Eg.) of benzyl bromide and 0.2 g of tetrabutylammonium iodide are added, the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for twenty four hours at 30° C.

9 g of the benzyl ester product in the title are obtained. Quantitative determination of the ester groups is carried out according to the method described on pages 169–172 of Siggia S. and Hanna J. G. "Quantitative organic analysis via functional groups" 4th Edition, John Wiley and Sons.

Example 13

Preparation of the β-phenylethyl Ester of Hyaluronic Acid (HY)

12.4 g of HY tetrabutylammonium salt with a molecular weight of 125,000 corresponding to 20 m.Eq. of a monomeric unit are solubilized in 620 ml of dimethylsulfoxide at 25° C., 4.6 g (25 m.Eq.) of 2-bromoethylbenzene and 185 mg of tetrabutylammonium iodide are added, and the solution is kept for 12 hours at 30° C.

The resulting mixture is slowly poured into 3,500 ml of ethyl acetate under constant agitation. A precipitate is thus formed which is then filtered and washed four times with 500 ml of ethyl acetate and finally vacuum dried for twenty four hours at 30° C.

9.1 g of the β-phenylethyl ester in the title are obtained. Quantitative determination of the ester groups is carried out according to the method described on page 168–172 of Siggia S. and Hanna J. G. "Quantitative organic analysis via functional groups" 4th Edition, John Wiley and Sons.

Example 14

Preparation of the Benzyl Ester of Hyaluronic Acid (HY)

3 g of the potassium salt of HY with a molecular weight of 162,000 are suspended in 200 ml of dimethylsulfoxide; 120 mg of tetrabutylammonium iodide and 2.4 g of benzyl bromide are added.

The suspension is kept in agitation for 48 hours at 30° C. The resulting mixture is slowly poured into 1,000 ml of ethyl acetate under constant agitation. A precipitate is formed which is filtered and washed four times with 150 ml of ethyl acetate and finally vacuum dried for twenty four hours at 30° C.

3.1 g of the benzyl ester product in the title are obtained. Quantitative determination of the ester groups is carried out according to the method described on pages 169–172 of Siggia S. and Hanna J. G. "Quantitative organic analysis via functional groups" 4th Edition, John Wiley and Sons.

Example 15

Preparation of the (Partial Propyl) Ester of Hyaluronic Acid (HY)—85% of Esterified Carboxylic Groups—15% of Salified Carboxylic Groups (Na)

12.4 g of HY tetrabutylammonium salt with a molecular weight of 165,1000 corresponding to 20 m.Eq. of a monomeric unit are solubilized in 620 ml of dimethysulfoxide at 25° C., 2.9 g (17 m.Eq.) of propyl iodide are added and the resulting solution is kept for 12 hours at 30° C.

A solution is then added containing 62 ml of water and 9 g of sodium chloride and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30° C.

The product is then dissolved in 550 ml of water containing 1.% of sodium chloride and the solution is slowly poured into 3,000 ml of acetone under constant agitation. A precipitate is formed which is filtered and washed twice with 500 ml of acetone/water 5:1 and three times with 500 ml of acetone and finally vacuum dried for 24 hours at 30° C. 8 g of the partial propyl ester compound in the title are obtained. Quantitative determination of the ester groups is carried out using the method of R. H. Cundiff and P. C. Markunas [Anal. Chem. 33, 1028–1030 (1961)].

Example 16

Preparation of the N-octyl Ester of Hyaluronic Acid (HY)

12.4 g of HY tetrabutylammonium salt with a molecular weight of 170.000 corresponding to 20 m.Eq. of a monomeric unit are solubilized in 620 ml of dimethylsulfoxide at 25° C., 4.1 g (21.2 m.Eq.) of 1-bromooctane are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9.3 g of the octyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

Example 17

Preparation of the Isopropyl Ester of Hyaluronic Acid (HY)

12.4 g of HY tetrabutylammonium salt with a molecular weight of 170.000 corresponding to 20 m.Eq. of a monomeric unit are solubilized in 620 ml of dimethylsulfoxide at 25° C., 2.6 g (21.2 m.Eq.) of isopropyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 8.3 g of the isopropyl ester product in the title are obtained. Quantitative determination of the ester groups is carried out using the method of R. H. Cundiff and P. C. Markunas (Anal. Chem. 33, 1028–1030, 1961).

Example 18

Preparation of the 2,6-dichlorobenzyl Ester of Hyaluronic Acid (HY)

12.4 g of HY tetrabutylammonium salt with a molecular weight of 170.000 corresponding to 20 m.Eq. of a monomeric unit are solubilized in 620 ml of dimethylsulfoxide at 25° C., 5.08 g (21.2 m.Eq.) of 2,6-dichlorobenzyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9.7 g of the 2,6-dichlorobenzyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

Example 19

Preparation of the 4-terbutylbenzyl Ester of Hyaluronic Acid (HY)

12.4 g of HY tetrabutylammonium salt with a molecular weight of 170,000 corresponding to 20 m.Eq. of a monomeric unit are solubilized in 620 ml of dimethylsulfoxide at 25° C., 4.81 g (21.2 m.Eq.) of 4-terbutylbenzyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9.8 g of the 4-terbutylbenzyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

Example 20

Preparation of the Heptadecyl Ester of Hyaluronic Acid (HY)

12.4 g of HY tetrabutylammonium salt with a molecular weight of 170,000 corresponding to 20 m.Eq. of a monomeric unit are solubilized in 620 ml of dimethylsulfoxide at 25° C., 6.8 g (21.2 M.Eq.) of Heptadecyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 11 g of the Heptadecyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

Example 21

Preparation of the Octadecyl Ester of Hyaluronic Acid (HY)

12.4 g of HY tetrabutylammonium salt with a molecular weight of 170,000 corresponding to 20 m.Eq. of a monomeric unit are solubilized in 620 ml of dimethylsulfoxide at 25° C., 7.1 g (21.2 m.Eq.) of octadecyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 11 g of the octadecyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

Example 22

Preparation of the 3-phenylpropyl Ester of Hyaluronic Acid (HY)

12.4 g of HY tetrabutylammonium salt with a molecular weight of 170,000 corresponding to 20 m.Eq. of a monomeric unit are solubilized in 620 ml of dimethylsulfoxide at 25° C., 4.22 g (21.2 m.Eq.) of 3-phenylpropyl bromide are added and the solution is kept for 12 hours at 3° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9 g of the 3-phenylpropyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

Example 23

Preparation of the 3,4,5-trimethoxy-benzyl Ester of Hyaluronic Acid (HY)

12.4 g of HY tetrabutylammonium salt with a molecular weight of 170,000 corresponding to 20 M.Eq. of a monomeric unit are solubilized in 620 ml of dimethylsulfoxide at 25° C., 4.6 g (21.2 m.Eq.) of 3,4,5-trimethoxybenzyl chloride are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 10 g of the 3,4,5-trimethoxybenzyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

Example 24

Preparation of the Cinnamyl Ester of Hyaluronic Acid (HY)

12.4 g of Hy tetrabutylammonium salt with a molecular weight of 170,000 corresponding to 20 m.Eq. of a monomeric unit are solubilized in 620 ml of dimethylsulfoxide at 25° C., 4.2 9 (21.2 m.Eq.) of Cinnamyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9.3 g of the Cinnamyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

Example 25

Preparation of the Decyl Ester of Hyaluronic Acid (HY)

12.4 g of HY tetrabutylammonium salt with a molecular weight of 170,000 corresponding to 20 m.Eq. of a monomeric unit are solubilized in 620 ml of dimethylsulfoxide at 25° C., 4.7 g (21.2 m.Eq.) of 1-bromo decane are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9.5 g of the Decyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

Example 26

Preparation of the Nonyl Ester of Hyaluronic Acid (HY)

12.4 g of HY tetrabutylammonium salt with a molecular weight of 170,000 corresponding to 20 m.Eq. of a monomeric unit are solubilized in 620 ml of dimethylsulfoxide at 25° C., 4.4 g (21.2 m.Eq.) of 1-bromo nonane are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9 g of the Nonyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

The Esters of Alginic Acid

The alginic acid esters which can be employed in the present invention can be prepared as described in EPA 0 251 905 A2 by starting with quaternary ammonium salts of alginic acid with an etherifying agent in a preferably aprotic organic solvent, such as dialkylsulfoxides, dialkylcarboxamides, such as in particular lower alkyl dialkylsulfoxides, above all dimethylsulfoxide, and lower alkyl dialkylamides of lower aliphatic acids, such as dimethyl or diethyl formamide or dimethyl or diethyl acetamide. It is possible, however, to use other solvents which are not always aprotic, such as alcohols, ethers, detones, esters, especially aliphatic or heterocyclic alcohols and ketones with a low boiling point, such as hexafluoroisopropanol and trifluoroethanol. The reaction is brought about preferably at a temperature of between about 0° and 100° C., and especially between about 25° and 75° C., for example at about 30° C.

Esterification is carried out preferably by gradually adding the esterifying agent to the above-mentioned ammonium salt dissolved in one of the solvents mentioned, for example in dimethylsulfoxide. As alkylating agents, those mentioned above can be used, especially hydrocarbyl halides, for example alkyl halides.

The preferred esterification process, therefore, comprises reacting, in an organic solvent, a quaternary ammonium salt of alginic acid with a stoichiometric quantity of a compound of the formula

A—X wherein A is selected from the group consisting of an aliphatic, araliphatic, cycloaliphatic, aliphatic-cycloaliphatic and heterocyclic radicals, and X is a halogen atom, and wherein said stoichiometric quantity of A—X is determined by the degree of esterification desired.

As starting quaternary ammonium salts, it is preferable to use lower ammonium tetraalkylates, the alkyl groups having preferably between 1 and 6 carbon atoms. Mostly, the alginate of tetrabutylammonium is used. These quaternary ammonium salts can be prepared by reacting a metal salt of alginic acid, preferably one of those mentioned above, especially the sodium or potassium salt, in aqueous solution with a sulfonic resin salified with the quaternary ammonium base.

One variation of the previously specified procedure consists of reacting a potassium or sodium salt of alginic acid, suspended in a suitable solution such as dimethylsulfoxide, with a suitable alkylating agent in the presence of a catalyzing quantity of a quaternary ammonium salt, such as tetrabutylammonium iodide. This procedure makes it possible to obtain the total esters of alginic acid.

To prepare new esters it is possible to use alginic acids of any origin. The preparation of these acids is described in literature. It is preferable to use purified alginic acids.

In the partial esters, it is possible to salify all the remaining carboxy groups or only part of these, dosing the base quantity so as to obtain the desired stoichiometric degree of salification. By correctly gauging the degree of salification, it is possible to obtain esters with a wide range of different dissociation constants, thereby giving the desired pH in solutions or "in situ" at the time of therapeutic application.

ALAFF 11, the benzyl ester of alginic acid, and ALAFF 7, the ethyl ester of alginic acid, are particularly useful in the present composite membranes.

For purely illustrative purposes, reported below are some examples of how composite membranes encompassed by the present invention can be produced, and how they can be employed in practice.

Example 27

A composite membrane comprising the hyaluronic acid benzyl ester HYAFF 11, i.e., hyaluronic acid esterified 100% with benzyl alcohol, with a mesh reinforcement comprising the hyaluronic acid ethyl ester HYAFF 7, i.e., hyaluronic acid esterified 100% with ethanol, basis weight 14 mg/cm$^2$, 0.25 mm thick, minimum tensile strength at break and elongation when dry, 400 Kg/cm$^2$ and 7%, respectively, minimum tensile strength and elongation when wet 50 Kg/cm$^2$ and 55%, respectively, tear strength when dry, 90 Kg/cm$^2$, tear strength when wet, 50 Kg/cm$^2$, was produced according to the following procedure.

The HYAFF 7 mesh was obtained starting with a solution of HYAFF 7 dimethylsulfoxide at a concentration of 125 mg/ml prepared in vessel (1) shown in FIG. 1. The solution is fed by a gear metering pump (2) into a spinneret for wet extrusion composed of 100 holes each measuring 65 microns in diameter.

Figure 2:
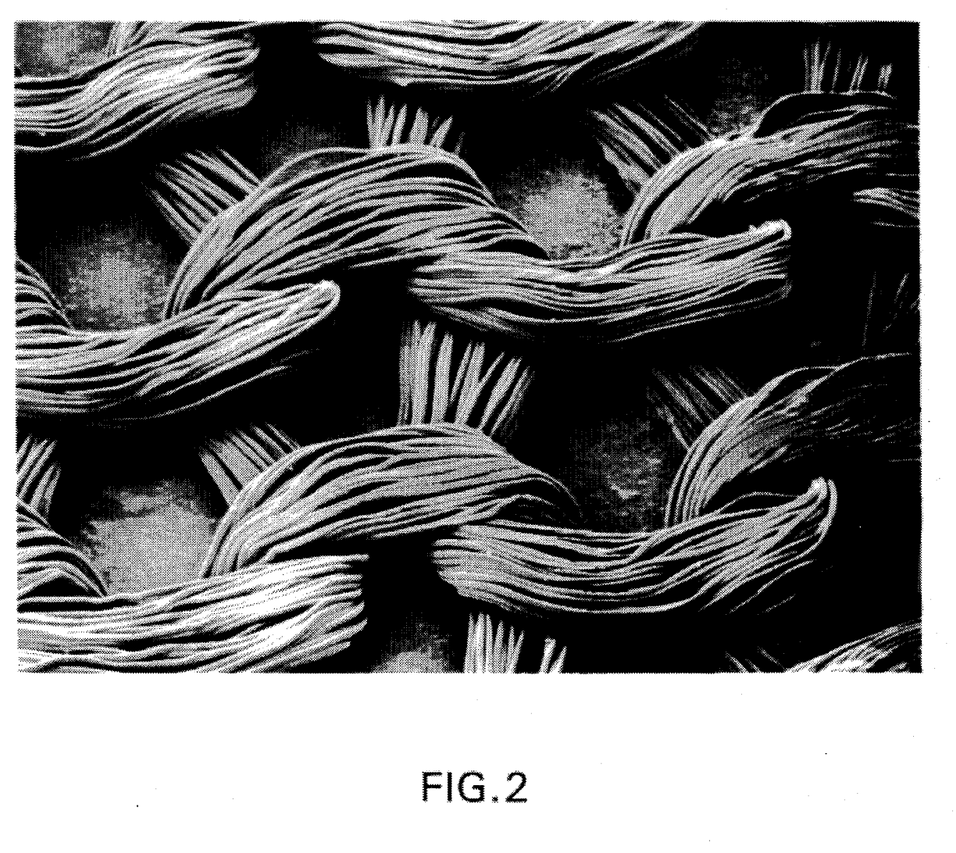
FIG. 2 shows the HYAFF 7 mesh which results from the process described in Example 27.

The extruded multiple thread is passed into a coagulation bath (3) containing absolute ethanol and is then moved over transporting rollers into three successive rinsing baths (4,5,6), also containing absolute ethanol. The ratio between the speed of the third roller (III) and the speed of the first roller (I) is called the drafting ratio, and has a value of 1.05, while the speeds of the single rollers are: 23 rpm (roller I), 24 rpm (rollers II and III), 25 rpm (roller IV). Once the multiple thread has been passed through the rinsing baths it is dried with warm air (7) at a temperature of 45° C. and wound onto a winding frame (8). The thread is 237 denier. The multiple thread is then twisted 135 times per meter and woven on a loom into a smooth knitted fabric with a gauge of 14 (9,10). From the loom the fabric is fed through a calendar (11), which thins it down. FIG. 2 shows the mesh which results from said process.

Figure 3:
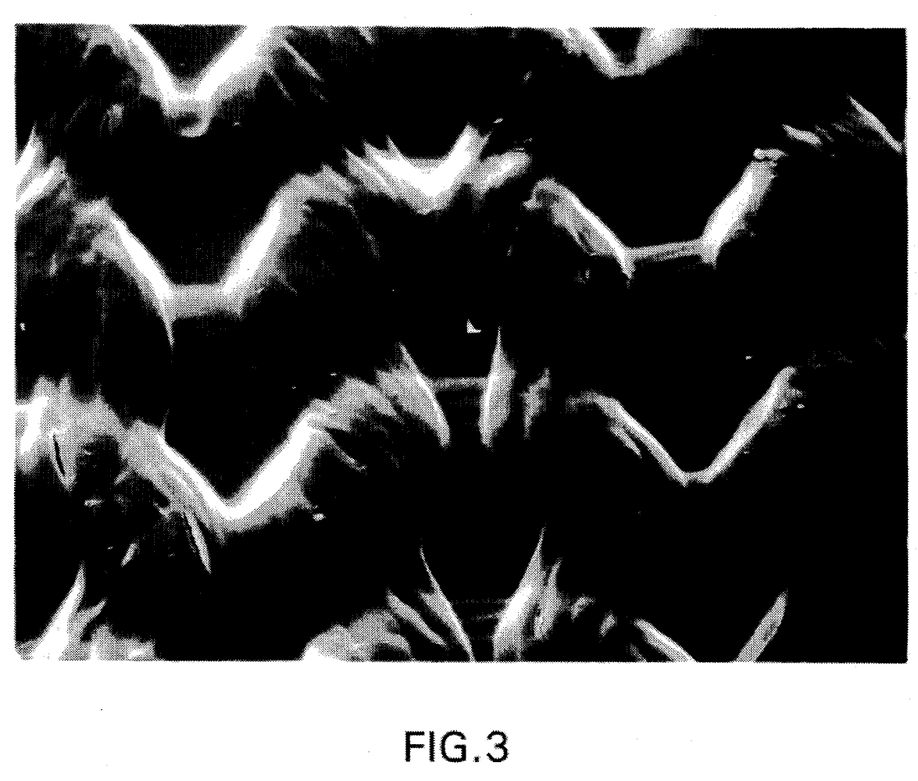
FIG. 3 shows the HYAFF 7 mesh shown in FIG. 2 after application of the HYAFF 11 polymeric matrix, as described in Example 27.

The polymeric matrix is applied by two airbrushes (14) which spray a solution of HYAFF 11 in dimethylsulfoxide at a concentration of 40 mg/ml. The mesh thus sprayed is passed into a coagulation bath (15) containing absolute ethanol, into a rinsing chamber containing pure, distilled water (6) and into a special drying chamber with a temperature of 50° C. (17). FIG. 3 shows the finished product.

Example 28

A reinforced membrane comprising a matrix of a partial benzyl ester (75%) of hyaluronic acid, HYAFF 11p75, with a mesh reinforcement comprising hyaluronic acid total benzyl ester HYAFF 11, basis weight 10 mg/cm$^2$, 0.15 mm thick, minimum tensile strength at break and elongation when dry, 300 Kg/cm$^2$ and 4%, respectively, minimum tensile strength at break and elongation when wet 40 Kg/cm$^2$ and 45%, respectively, tear strength when dry 120 Kg/cm$^2$, and when wet 60 g/cm$^2$, was produced by the following procedure.

HYAFF 11p75 is prepared as follows. 10 g of hyaluronic acid tetrabutylammonium salt, mw=620.76, equal to 16.1 nmole, are solubilized in a mixture of N-methyl pyrrolidone/H$_2$O, 90/10, 2.5% in weight, to obtain 400 mls of solution. The solution is cooled to 10° C., then purified N$_2$ is bubbled through it for 30 minutes. This is then esterified with 1.49 ml (equal to 12.54 mmole) of benzyl bromide. The solution is gently shaken for 60 hours at 15°–20° C.

Subsequent purification is achieved by precipitation in ethyl acetate following the addition of a saturated solution of sodium chloride, and subsequent washings with a mixture of ethyl acetate/absolute ethanol, 80/20. The solid phase is separated by filtration, and treated with anhydrous acetone. 6.8 g of product are thus obtained, equal to a yield of about 95%.

The HYAFF 11 mesh was produced starting from a solution of HYAFF 11 in dimethylsulfoxide at a concentration of 145 mg/ml prepared in vessel (1) shown in FIG. 1. The solution is fed by a gear metering pump (2) into a spinneret for wet extrusion composed of 70 holes each measuring 50 microns in diameter. The extruded multiple thread is passed into a coagulation bath (3) containing 90% absolute ethanol and 10% pure, distilled water, and is then moved over transporting rollers into three successive rinsing baths (4,5,6) these also containing 90% absolute ethanol and 10% pure, distilled water. The ratio between the speed of the third roller (III) and the speed of the first roller (I) is called the drafting ratio, and has a value of 1.03, while the speeds of the single rollers are: 20 rpm (roller I), 21 rpm (rollers II and III), 22 rpm (roller IV). Once the multiple thread has been passed through the rinsing baths it is dried with warm air (7) at a temperature of 47° C. and wound onto a winding frame (8). The resulting thread is 150 denier. The multiple thread is then twisted 90 times per meter and woven on a loom into a smooth knitted fabric with a gauge of 12 (9,10). From the loom the fabric is fed through a calendar (11) which thins it down.

The polymeric matrix is applied by two airbrushes (14) which spray the mesh with a solution of HYAFF 11p75 in dimethylsulfoxide at a concentration of 30 mg/ml. The mesh thus sprayed is passed into a coagulation bath (15) containing absolute ethanol, into a rinsing chamber containing pure, distilled water (16) and into a special drying chamber with a temperature of 45° C. (17).

Example 29

A composite membrane comprising a matrix of a partial benzyl ester (75%) of hyaluronic acid, HYAFF 11p75, with a mesh reinforcement comprising a mixture of fibers of hyaluronic acid total benzyl ester, HYAFF 11, and alginic acid benzyl ester, ALAFF 11, in equal percentages, basis weight 16 mg/cm$^2$, 0.25 mm thick, minimum tensile strength at break and elongation when dry, 350 Kg/cm$^2$ and 5%, respectively, minimum tensile strength at break and elongation when wet, 100 Kg/cm$^2$ and 35%, respectively, tear strength when dry 110 Kg/cm$^2$, and when wet, 70 Kg/cm$^2$, was produced by the following procedure.

Alginic acid benzyl ester ALAFF 11 was prepared as described in U.S. Pat. No. 5,147,861 and EPA 0 251 905 A2. 10 g (23.9 m.Eq.) of the tetrabutylammonium salt of alginic acid are solubilized in 400 ml of DMSO at 25° C. 4.45 g (26 m.Eq.) of benzyl bromide and 0.1 g of tetrabutylammonium iodide are added.

The solution is agitated well for 12 hours at 30° C., and then slowly poured by regular drops and under agitation into 3.5 l of ethyl acetate (or toluene). The precipitate is filtered and then washed 4 times with ethyl acetate, and vacuum dried for 24 hours at 30° C. In this way, 5 g of the compound are obtained.

The mesh formed from a multiple thread of HYAFF 11 and ALAFF 11 in equal percentages was obtained starting from two distinct multifilaments, one of HYAFF 11 at 60 denier, and the other of ALAFF 11 at 75 denier.

The multifilament of HYAFF 11 was obtained as described in Example 2, while the multifilament of ALAFF 11 was obtained as follows. A solution of ALAFF 11 in dimethylsulfoxide at a concentration of 100 mg/ml is prepared in vessel (1) shown in FIG. 1. The solution is fed by a gear metering pump (2) into a spinneret for wet extrusion composed of 35 holes, each measuring 50 microns in diameter. The extruded multiple thread is passed into a coagulation bath (3) containing 45% absolute ethanol, 45% ethyl acetate and 10% pure, distilled water. It is then moved over transporting rollers into three successive rinsing baths (4,5,6) containing acetone. The ratio between the speed of the third roller (III) and the speed of the first roller (I) is called the drafting ratio, and has a value of 1.1, while the speeds of the single rollers are: 20 rpm (roller I), 21 rpm (rollers II and III), 22 rpm (roller IV). Once the multiple thread has been passed through the rinsing baths it is dried with warm air (7) at a temperature of 55° C. and wound onto a winding frame (8). The 60 denier HYAFF 11 thread and the 75 denier ALAFF 11 thread are combined on a twisting machine, producing a multifilament of HYAFF 11 and ALAFF 11. This is then twisted 90 times per meter and woven on a loom into a smooth knitted fabric with a gauge of 12 (9,10). From the loom the fabric is fed through a calendar (11) which thins it down.

The polymeric matrix is applied by two airbrushes (14) which spray a solution of HYAFF 11p75 in dimethylsulfoxide at a concentration of 30 mg/ml. Thus sprayed, the mesh is passed into a coagulation bath (15) containing absolute ethanol, into a rinsing chamber containing pure, distilled water (16) and into a special drying chamber with a temperature of 45° C. (17).

Example 30

The mechanical and biological advantages of the composite membranes according to the present invention have been demonstrated by a series of clinical and periodontal surgical experiments conducted using the material described in Example 1 according to standard guided tissue regeneration (GTR) protocols. Such protocols require the material to be placed following suitable surgical techniques by suturation to the site of application to enhance the formation of new tissues to replace those damaged or destroyed by various periodontal pathologies.

Such lesions have in common the loss of the original structure of periodontal tissue and introflexion into the cavities thus formed in the mucogingival tissue. This leads to imperfect healing with debilitating effects on the function, structure and stability of the dental elements involved. Two types of defects were studied. The first involved periradicular lesions of various kinds (to one or more walls, partially or completely exposed bifurcations, circular or semicircular defects). The second type involved bone ridges that are too fine to support a normal tooth replacement or the insertion of an implant. Reference values included the intactness of the reinforced membrane at the site and at the time of its application (maximum intactness is defined as +++), inflammation of the tissues above the membrane (maximum inflammation is defined as +++), reduction in the defect thirty days after surgery (maximum reduction is defined as +++), and reabsorption of the inserted material (maximum reabsorption is defined as +++). Table 2 shows examples of data relative to surgical operations on humans in clinical experiments using composite membranes such as those described in Example 27.

The results presented in Table 2 show that the composite membranes according to the present invention successfully associate biocompatibility, bioabsorbability and biodegradability with a high degree of mechanical resistance. This combination of properties is not present in other products used for the same application in periodontal surgery, demonstrating the superiority of the present composite membranes over conventional products.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A composite membrane, comprising a reinforcing mesh embedded in and chemically linked to a polymeric matrix, wherein said mesh comprises fibers selected from the group consisting of fibers of a hyaluronic acid ester, and a combination of fibers of a hyaluronic acid ester and an alginic acid ester, and said polymeric matrix comprises a material selected from the group consisting of a hyaluronic acid ester, alginic acid, an alginic acid ester, and a gelled polysaccharide.

2. The composite membrane of claim 1, wherein the alcohol of said hyaluronic acid ester or said alginic acid ester is a pharmacologically inactive alcohol.

3. The composite membrane of claim 2, wherein said alcohol is an aliphatic, araliphatic, cycloaliphatic, or heterocyclic alcohol.

4. The composite membrane of claim 1, wherein said gelled polysaccharide is a member selected from the group consisting of chitin, an alginate, chitosan, gellan, a synthetic derivative of any one of the foregoing, a semisynthetic derivative of any one of the foregoing, and mixtures thereof.

5. The composite membrane of claim 1, wherein the alcohol of said hyaluronic acid ester or said alginic acid ester is a pharmacologically active alcohol.

6. The composite membrane of claim 1, wherein said reinforcing mesh comprises a multifilament mesh comprising multiple threads of about 70 strands, wherein the thread is about 150 denier, and wherein the multifilaments are twisted about 90 times per meter, and which is worked into a knitted fabric with a gauge of about 12.

TABLE 2

| CASE | TYPE OF OPERATION | INTACTNESS | INFLAMATION | REDUCTION IN DEFECT (30 DAYS) | REABSORPTION |
| --- | --- | --- | --- | --- | --- |
| CASE 1 | 1 | +++ | +-- | ++- | ++- |
| CASE 2 | 1 | +++ | ++- | ++- | ++- |
| CASE 3 | 1 | +++ | +-- | +++ | +++ |
| CASE 4 | 1 | +++ | +-- | ++- | ++- |
| CASE 5 | 1 | +++ | +-- | +++ | +++ |
| CASE 6 | 1 | +++ | +-- | ++- | ++- |
| CASE 7 | 1 | +++ | ++- | ++- | ++- |
| CASE 8 | 1 | +++ | +-- | +++ | +++ |
| CASE 9 | 1 | +++ | +-- | ++- | ++- |
| CASE 10 | 1 | +++ | +-- | ++- | ++- |
| CASE 11 | 1 | +++ | ++- | ++- | ++- |
| CASE 12 | 1 | +++ | +-- | ++- | ++- |
| CASE 13 | 2 | +++ | ++- | +++ | ++- |
| CASE 14 | 2 | +++ | ++- | ++- | +-- |
| CASE 15 | 2 | +++ | +++ | +-- | +-- |
| CASE 16 | 2 | +++ | ++- | ++- | +-- |
| CASE 17 | 2 | +++ | ++- | ++- | ++- |

1 = PERIRADICULAR LESION
2 = BUILD UP OF BONE RIDGE

7. The composite membrane of claim 1, wherein said reinforcing mesh comprises fibers of a single hyaluronic acid ester or fibers of a mixture of different hyaluronic acid esters.

8. The composite membrane of claim 1, wherein said reinforcing mesh comprises fibers of a single alginic acid ester or fibers of a mixture of different alginic acid esters.

9. The composite membrane of claim 1, wherein said reinforcing mesh comprises fibers of a mixture of a hyaluronic acid ester and an alginic acid ester.

10. The composite membrane of claim 1, wherein said reinforcing mesh comprises fibers of a mixture of hyaluronic acid esters and alginic acid esters.

11. The composite membrane of claim 1, wherein said reinforcing mesh comprises fibers of a mixture of hyaluronic acid esters, alginic acid esters, and a gelled polysaccharide selected from the group consisting of chitin, an alginate, chitosan, gellan, a synthetic derivative thereof, a semisynthetic derivative thereof, and mixtures thereof.

12. The composite membrane of claim 1, wherein both said fibers of said reinforcing mesh and said matrix comprise hyaluronic acid or a derivative thereof.

13. The composite membrane of claim 12, wherein said derivative is a hyaluronic acid ester.

14. The composite membrane of claim 13, wherein said reinforcing mesh comprises fibers of the ethyl ester of hyaluronic acid, and said matrix comprises the benzyl ester of hyaluronic acid.

15. The composite membrane of claim 13, wherein said reinforcing mesh comprises fibers of the benzyl ester of hyaluronic acid, and said matrix comprises a partial benzyl ester of hyaluronic acid.

16. The composite membrane of claim 15, wherein said partial benzyl ester of hyaluronic acid is a 75% benzyl ester of hyaluronic acid.

17. The composite membrane of claim 13, wherein said reinforcing mesh comprises fibers of the ethyl ester of hyaluronic acid, and said matrix comprises a partial benzyl ester of hyaluronic acid.

18. The composite membrane of claim 17, wherein said partial benzyl ester of hyaluronic acid is a 75% benzyl ester of hyaluronic acid.

19. The composite membrane of claim 1, wherein said mesh comprises a mixture of fibers of hyaluronic acid benzyl ester and fibers of alginic acid benzyl ester, and said matrix comprises a partial benzyl ester of hyaluronic acid.

20. The composite membrane of claim 19, wherein said fibers are present in equal amounts, and wherein said partial benzyl ester of hyaluronic acid is a 75% benzyl ester of hyaluronic acid.

21. The composite membrane of claim 1, having a basis weight between about 8 g/cm$^2$ and about 50 g/cm$^2$, a gauge of about 0.08 mm to about 0.5 mm, a minimum tensile strength at break when dry between about 100 Kg/cm$^2$ and about 500 Kg/cm$^2$, elongation when dry between about 3% and about 12%, a minimum tensile strength at break when wet between about 30 Kg/cm$^2$ and about 450 Kg/cm$^2$ and elongation when wet between about 20% and about 60%, and a tear strength when dry between about 40 Kg/cm$^2$ and about 200 Kg/cm$^2$ and tear strength when wet between about 20 Kg/cm$^2$ and about 160 Kg/cm$^2$.

22. The composite membrane of claim 1, having a basis weight of about 14 mg/cm$^2$, a gauge from about 0.25 mm, a minimum tensile strength at break when dry from about 400 Kg/cm$^2$, elongation when dry, about 7%, a minimum tensile strength at break when wet from about 50 Kg/cm$^2$ and elongation when wet, about 55%, with a tear strength when dry, about 90 Kg/cm$^2$ and tear strength when wet, about 50.

23. The composite membrane of claim 1, having a basis weight of about 10 mg/cm$^2$, a gauge from about 0.15 mm, a minimum tensile strength at break when dry from about 300 Kg/cm$^2$, elongation when dry, about 4%, a minimum tensile strength at break when wet from about 40 Kg/cm$^2$ and elongation when wet, about 45%, with a tear strength when dry, about 120 Kg/cm$^2$ and tear strength when wet, about 60.

24. The composite membrane of claim 1, wherein said reinforcing mesh comprises a multifilament mesh comprising multiple threads of between about 30 and about 120 strands between about 18 microns and about 35 microns in diameter, wherein the thread is between about 150 and about 400 denier, wherein the multifilaments are twisted between about 90 and about 200 times per meter, and which is worked into a knitted fabric with a gauge between about 10 and about 16.

25. The composite membrane of claim 1, wherein said reinforcing mesh comprises a multifilament mesh comprising multiple threads of at least 100 strands, wherein the thread is about 237 denier, and wherein the multifilaments are twisted about 135 times per meter, and which is worked into a knitted fabric with a gauge of about 14.

26. A composite membrane, comprising a reinforcing mesh embedded in and chemically linked to a polymeric matrix, wherein said reinforcing mesh comprises fibers of a partial hyaluronic acid ester, and said polymeric matrix comprises a partial hyaluronic acid ester.

27. The composite membrane of claim 26, wherein said reinforcing mesh comprises a partial benzyl ester of hyaluronic acid, and said polymeric matrix comprises a partial benzyl ester of hyaluronic acid.

* * * * *